[19] United States Patent
Wilson et al.

[11] Patent Number: 5,780,381
[45] Date of Patent: Jul. 14, 1998

[54] COBALT/MOLYBDENUM/ZIRCONIUM CATALYST FOR FISCHER-TROPSCH SYNTHESIS

[75] Inventors: Geoffrey Robert Wilson, Kit Tanning; Norman Loren Carr, Wexford, both of Pa.

[73] Assignee: Syncrude Technology Inc., Pittsburgh, Pa.

[21] Appl. No.: 711,972

[22] Filed: Sep. 10, 1996

Related U.S. Application Data

[63] Continuation-in-part of Ser. No. 356,697, Dec. 15, 1994, abandoned, and Ser. No. 485,351, Jun. 7, 1995, Pat. No. 5,639,798.

[51] Int. Cl.$^6$ ................................................ B01J 23/28
[52] U.S. Cl. ...................... 502/308; 502/314; 502/321; 502/322; 518/714; 518/715
[58] Field of Search .......................... 502/308, 314, 502/321, 322; 518/714, 715

[56] References Cited

U.S. PATENT DOCUMENTS

| | | | |
|---|---|---|---|
| 3,840,473 | 10/1974 | Beuther et al. | 252/439 |
| 4,019,976 | 4/1977 | Cosyns et al. | 208/57 |
| 4,555,526 | 11/1985 | Wakui et al. | 518/717 |
| 4,579,830 | 4/1986 | Coughlin | 502/66 |
| 4,613,624 | 9/1986 | Beuther et al. | 518/715 |
| 5,116,879 | 5/1992 | Eri et al. | 518/716 |
| 5,169,822 | 12/1992 | Weissman et al. | 502/255 |

*Primary Examiner*—Shrive Beck
*Assistant Examiner*—Timothy Meeks
*Attorney, Agent, or Firm*—Douglas Baldwin

[57] ABSTRACT

A catalyst for a slurry reactor Fischer-Tropsch conversion process utilizing novel catalysts comprising cobalt promoted with zirconium, molybdenum or zirconium and molybdenum and on a small diameter alumina support. The catalysts have been found to be highly selective for production of liquid hydrocarbons while minimizing production of less desirable oxygen-containing products such as alcohols. The preferred catalysts contain from about 5% to 35% cobalt and from about 0.1% to 10% zirconium or zirconium and molybdenum. The preferred process is carried out in a one or more slurry bubble column reactor stagesin series.

15 Claims, No Drawings

COBALT/MOLYBDENUM/ZIRCONIUM CATALYST FOR FISCHER-TROPSCH SYNTHESIS

This application is a continuation in part of U.S. application Ser. No. 08/356,697 filed Dec. 15, 1994, now abandoned, and U.S. application Ser. No. 08/485,351 filed Jun. 7, 1995, now U.S. Pat. No. 5,639,798.

BACKGROUND OF THE INVENTION

This invention relates to catalysts having improved activity and selectivity for the production of liquid hydrocarbons from hydrogen and carbon monoxide and to an improved hydrocarbon synthesis process. Specifically, this invention relates to a catalyst for use in an improved slurry reactor process comprising cobalt supported on alumina promoted by zirconium, molybdenum or zirconium and molybdenum.

Conversion of mixtures of carbon monoxide and hydrogen, for example synthesis gas "syngas") to hydrocarbons, is commonly referred to as Fischer-Tropsch synthesis. Fischer-Tropsch synthesis was used extensively in Germany during World War II. There is now considerable incentive for use of the process in the conversion of coal to liquid fuels and for conversion of natural gas to liquid fuels. Clean liquid fuels are more easily transported and utilized than coal. Conversion of natural gas to liquid hydrocarbons makes transportation and storage more feasible. Sasol operates commercial Fischer-Tropsch plants in South Africa which employ an iron catalyst (see for example *Oil and Gas Journal*, Jan. 20, 1992, p. 53). A large commercial plant using Shell's technology has been recently placed in production in Malaysia. These commercial operations typically employ fixed-bed reactor systems.

Slurry phase reactors, especially slurry bubble column reactor systems (SBCR), for Fischer-Tropsch processes have received considerable attention in recent years. The slurry process has a number of advantages, including the ability of the reactor to handle the large heats of reaction and with control of reaction temperature, the ability of iron catalysts to convert low $H_2/CO$ ratio synthesis gas without the need for a separate water-gas shift process step; and expected relatively low capital and operating costs. (See *Hydrocarbon Processing*, "Catalysts for Fischer-Tropsch," February 1990 pp. 59–68.) The term "slurry phase" and "slurry phase reactor" is used herein to mean mobile gas-liquid-solid phases used as a means for carring out a solid-phase catalytic reaction of a normally gas phase reactant(s) that is soluable in the liquid phase in direct contact with the porous solid catalyst. It is not simply a "slurry phase". Slurry reactor systems are characterized by suspending the Fischer-Tropsch catalyst in an upflow of synthesis gas in a suitable liquid medium. Basically, the process includes a finely divided catalyst suspended in oil that is mixed in a reactor (e.g. a SBCR) in the presence of synthesis gas. Early patents describing slurry processes are U.S. Pat. Nos. 2,438,029; 2,680,126; 2,852,350 and others. Slurry reactor systems are discussed in the article "Fischer-Tropsch Synthesis in the Slurry Phase," M. D. Schlesinger et al., *Industrial Engineering Chemistry*, Vol. 6, p. 1474 (1951). U.S. Pat. No. 4,252,736 discloses a process in which syngas is continuously bubbled through a column of Fischer-Tropsch catalyst suspended in oil.

In principle, all catalysts that are active for Fischer-Tropsch synthesis can be used in a Slurry Bubble Column Reactors (SBCR). The objective of catalyst choice is to obtain the highest possible selectivity of desired liquid hydrocarbon products with an active and stable catalyst. Iron catalysts have been employed because of low cost and good activity. However, better catalyst-reactor systems are desired.

Common Fischer-Tropsch catalysts are cobalt and iron (see for example, "The Fischer-Tropsch Synthesis," by R. B. Anderson, *Academic Press* (1984), p. 2). Other Group VIII metals such as ruthenium and osmium are also active. Other single metals that have been investigated as catalysts include rhenium, molybdenum, and chromium, but these have no or low activity and produce primarily methane. U.S. Pat. No. 5,162,284 to Soled et al. describes a copper promoted cobalt manganese spinel catalyst.

The activity of supported cobalt catalysts can be enhanced, or the performance modified, by the addition of a variety of metals. Exemplary metals include copper (U.S. Pat. Nos. 5,302,622 and 5,162,284), cerium (U.S. Pat. Nos. 3,888,792; 4,657,885; 4,801,573 and 4,880,763), rhenium (U.S. Pat. Nos. 4,088,671; 4,558,030; 4,568,663; 4,801,573 and 4,880,763) and manganese (U.S. Pat. No. 5,162,284). Precious metals include platinum, iridium, ruthenium and rhodium (U.S. Pat. Nos. 5,302,622; 5,059,574 and 5,102,851). In addition to enhancing catalyst activity, promoters are added to achieve specific purposes, e.g., to enhance liquid hydrocarbon production, to suppress methane production, etc. See for example the discussion in U.S. Pat. No. 4,880,763.

U.S. Pat. No. 5,302,622 to Chaumette, et al. references French Patent Application No. 91/07,634 that describes a supported three metal catalyst containing cobalt, at least one additional element chosen from molybdenum and tungsten and at least one element chosen from elements including ruthenium and copper.

Supports other than the alumina have been extensively investigated and successfully developed.

A series of Shell patents (e.g. U.S. Pat. Nos. 4,522,939; 4,499,209; 4,587,008 and 4,686,238) disclose silica supported cobalt catalysts containing zirconium, titanium or chromium. These patents disclose in a very general way the use of the promoting metals on various supports but only discuss silica catalysts. These catalysts are designed for fixed bed operation and depend on effectiveness on the specific nature of metal incorporation on the support, i.e., by impregnation and/or kneading the large particles to produce an egg-shell effect.

U.S. Pat. Nos. 4,801,573 and 4,880,763 recite the use of small amounts of promoter oxides chosen from elements in Groups IIIB, IVB and VB (including zirconia) but no promotional effect on either activity or selectivity was shown.

Coughlin, in U.S. Pat. No. 4,579,830 discloses a zeolite supported cobalt catalyst that may be promoted with molybdenum or tungsten and preferably with thorium to produce light olefinic hydrocarbons predominantly in the $C_1$ to $C_9$ range.

In view of the known tendency of molybdenum containing catalysts to lower Fischer-Tropsch synthesis activity and to increase methane production and the use of molybdenum as a promoter only with additional promoters, it was surprising to discover that catalysts comprising cobalt supported on an alumina could be effectively promoted to higher activity and improved liquid hydrocarbon selectivity by incorporation of zirconium, molybdenum and/or zirconium together with molybdenum. This invention provides such an improved catalyst used in a three phase SBCR reactor and an improved process for Fischer-Tropsch synthesis.

SUMMARY OF THE INVENTION

It has been unexpectedly found that the addition of zirconium, molybdenum or zirconium together with molybdenum on an alumina support substantially increases the effectiveness of cobalt catalysts useful for the conversion at reaction conditions of synthesis gas to hydrocarbons in a slurry reaction process. The process utilizing these catalysts has been found to be highly selective for production of liquid hydrocarbons while minimizing production of less desirable light hydrocarbon gases and oxygen-containing products such as alcohols, giving selectivities of $C_5$ plus hydrocarbons in excess of 80%. The catalysts contain from about 5% wt. to 35% wt. cobalt and from about 0.1% wt. to 10% wt. zirconium, molybdenum or molybdenum and zirconium based on the total weight of the catalyst, the weight ratio of zirconium (or molybdenum or a mixture of both zirconium and molybdenum) to cobalt being from about 0.03 to 0.20 and the support having a particle size range of about 5 to 250 microns. The process comprises use of the above catalysts in a slurry reactor process, specifically a bubble column slurry reactor system, and preferably a two stage reactor system with interstage removal of liquid product hydrocarbons and water.

Other advantages and features will be apparent from the following description and from the claims.

DESCRIPTION OF THE PREFERRED EMBODIMENTS

The catalysts of the present invention comprise cobalt supported on an alumina support which catalyst is promoted with zirconium, molybdenum or zirconium and molybdenum. The preferred catalyst contains both zirconium and molybdenum. These catalysts have been found to have high activity for the conversion of synthesis gas with high selectivity to liquid hydrocarbons up to the $C_{50}$ plus range. Specifically these catalysts produce $C_5$ plus selectivities in excess of 80%. The observed Schulz-Flory alpha values are high corresponding to high potential yields of middle distillates. Unlike catalyst systems such as that of Coughlin, U.S. Pat. No. 4,579,830 that produce olefinic hydrocarbons in the $C_2$ to $C_9$ range, the present catalysts produce predominately heavier hydrocarbons as well.

Cobalt is added to an alumina support in amounts up to 35 wt. % of the final catalyst. Preferably, amounts between 5 and 25 wt. %; more preferably amounts between 8 and 25 wt. %, and most preferably between 10 and 20 wt. % are employed. The amount of zirconium or molybdenum is preferably between 0.1 and 10 wt. %, and more preferably between 1 and 8 wt. %. It is preferred the ratio of zirconium or molybdenum (or combination of zirconium and molybdenum) to cobalt be below about 0.150 and more preferably below about 0.125. In this way the catalyst is distinguished from prior art hydrosulfurization catalysts which do not work as effective Fischer-Tropsch catalysts. The support has a high surface area to more effectively disperse the catalytic components. The surface area is preferably greater than about 50 $m^2/g$, and the pore volume is preferably greater than 0.4 ml/g. Alumina particularly suitable for the support may be in any of the crystallographic forms such as gamma, eta, xi, theta, delta, kappa or mixtures thereof. X-ray amorphous aluminas, such as those derived by high temperature activation of alumina trihydrates such as gibbsite, are also suitable. Gamma alumina or anhydrous alumina derived from LaRoche VERSAL 900 psuedoboehmite alumina are especially preferred. VERSAL is a trademarked pseudoboehmite alumina available from LaRoche Chemicals. Silica/alumina and/or zeolite supports or other acidic supports give rise to cracking of the hydrocarbons produced and yield a more olefinic and lower carbon range product. For the preferred slurry process of this invention, the alumina support is in the form of microspheres with a particle size range of 5 to 250 microns, more preferably 5 to 100 microns, and most preferably, 10 to 75 microns. The microspheres can be made in any suitable manner known in the art, but are usually prepared by spray drying a liquid solution of suitable aluminum compound through a spray nozzle sized and operated to provide the desired spherical shaped dried pellets.

Catalyst Preparation

The catalytic metals are incorporated on the support by any suitable known methods. Impregnation is accomplished either by the incipient wetness method or by using an excess of impregnating solution followed by evaporation of the excess liquid. It is preferred that impregnation be made from aqueous solutions of water soluble salts of the metals. Aqueous solutions of water soluble metal salts such as cobalt or zirconium nitrates, acetates or chlorides are suitable as is ammonium salts of the metals such as ammonium molybdate.

The catalytic metals can be applied either separately or from a common solution. It is preferred that they be applied from a common solution, i.e., co-impregnated. Co-impregnation from a common aqueous solution to obtain a homogeneous impregnation of the metals on the support is especially preferred. Other special impregnation techniques such as layered impregnation of different metals or layers of metals are not required. When applied separately, the support is dried after impregnation at a temperature between 80° and 130° C. for several hours to remove the excess water. The catalyst is similarly dried after the final impregnation, usually for a period of at least 4 hours but typically overnight. The catalyst may be calcined in either air or hydrogen prior to use. If calcination in air is first performed prior to reduction in hydrogen, temperatures are suitably 250° to 550° C. and preferably 300° to 350° C. for both calcination and reduction. Hydrogen calcination is preferred.

Before use, the catalyst is activated in flowing hydrogen in a fluidized bed. This is done in a reduction apparatus in which hydrogen is passed up-flow through the catalyst at an elevated temperature. The reduction is carried out at atmospheric pressure or at elevated pressure. Low pressure is preferred to minimize the effect of water on the catalyst. The temperature of the catalyst in the reduction unit is increased at a rate of between 0.5 and 2° C./min from ambient to a final level of between 250° and 450° C.: preferably between 300° and 400° C., and more preferably between 325° and 375° C. and maintained at the maximum temperature for about 6 to 24 hours, more preferably 10 to 24 hours.

After reduction, the catalyst may be partially re-oxidized in a diluted oxygen-containing atmosphere to "passivate" or reduce its tendency to be pyrophoric. If passivated, the catalyst is re-reduced, at conditions similar to those described above, prior to use in the process. The reduced catalyst is suitably protected from re-oxidation prior to introduction into the slurry reactor. A convenient protection method is to cover the catalyst with a high molecular weight hydrocarbon such as Chevron Synfluid or liquid product from a Fischer-Tropsch process.

Process

In general, three reactor configurations, such as fixed bed, fluidized bed, or slurry type reactors, well known to those skilled in the art, are suitable for the Fischer-Tropsch synthesis.

The process of this invention is a slurry reactor system, and the catalysts of this invention are particularly suited for slurry phase process application, particularly a process using a slurry bubble column reactor (SBCR) system. For the slurry bubble column (SBCR) reactor system the catalysts have a particle size range of 5 to 250 microns, more preferably in the range of 5 to 100 microns, and most preferably in the range of 10 to 75 microns. The catalyst supports must be small particles but it is highly preferred that they be microspheres for use in the SBCR system. The particle sizes, of cource, refer to the initial size prior to use in the SBCR system. During and after use the catalyst sizes may change by attrition and/or agglomerization.

The slurry process offers a number of advantages in addition to being particularly suitable with the promoted catalysts of this invention, including better control of the removal of exothermic heat produced in the Fischer-Tropsch synthesis and provides better control over catalyst activity maintenance by allowing continuous liquid recycle, catalyst make-up and removal, recovery and rejuvenation while on stream.

The slurry reaction system comprises a suitable catalyst suspended in a liquid medium suitable for the purpose of converting syngas to hydrocarbons products. Basically, the slurry catalyst process constitutes a process in which the small diameter or finely divided catalyst having a particle size of about 5 to 75 microns is mixed in oil is suspended by synthesis gas up-flow through a reactor. The bubble column slurry process is a process in which syngas is continuously bubbled through a column of catalyst suspended in oil.

A carbon monoxide/hydrogen mixture is forced through the catalyst slurry in a manner and at a rate to allow intimate contact between the $CO/H_2$ and catalyst slurry. The process is operated in either a batch or continuous liquid recycle. In the continuous recycle mode, only a product liquid is circulated in the system. The slurry liquid used in the process is a liquid at reaction temperatures and must be chemically inert under reaction conditions. It must also be a relatively good solvent for $CO/H_2$ and possess good slurrying, dispersion and suspension properties for the finely divided catalyst. Representative classes of organic liquids that can be used for start-up include high boiling paraffins and aromatic hydrocarbons. High boiling paraffins include $C_{10}$–$C_{50}$ linear or branched paraffin; the aromatic hydrocarbons include $C_{10}$–$C_{20}$ single ring and multiple ring aromatics.

After start-up vehicle liquids are depleted, the product wax ($C_{20}$ plus hydrocarbons) become the indigenous liquid medium.

The slurry liquid can contain substantially no S, P, As or Sb, since these elements are poisons in the slurry process. Specific liquids are dodecane, tetradecane, hexadecane, octadecane, cosane, tetracosane, tetracosane, tetracosane, and the like. Octacosane and hexadecane are particularly suitable, as are certain commercially available liquid hydrocarbons such as Chevron Synfluid, a product made available from Chevron Chemical Company, and Fischer-Tropsch wax.

The concentration of fresh catalyst used in the liquid hydrocarbon slurry solvent is generally about 10 to 100 grams of dry catalyst per 500 grams of slurry; preferably, about 30 to 50 grams dry catalyst per 500 grams slurry, i.e., 50 to 85 grams per liter.

A two-reactor process system is especially preferred. In the two stage reactor process two reactors are used with intermediate by-product water and hydrocarbon liquid products are removed from the process stream between the two reactors. Process conditions in each of the reactors may be as outlined above for a single reactor. In this process CO and hydrogen are introduced into the first reactor at conditions outlined above. Hydrocarbon product and water (produced by the reaction) are removed by suitable means well known in the art (flashing, distillation and the like) and the unreacted CO and hydrogen are introduced into the second reactor. More than two reactor stages can also suitably be used. This two (or more) stage process has a number of advantages including:

1.) the overall reactor volume requirements to achieve a given conversion can be reduced by one over the number of reactors, e.g. by ½ for a two reactor system.
2.) the catalyst requirement is likewise reduced.
3.) the activity stability is greatly enhanced.
4.) the $C_5$ plus selectivity is increased and the CO2 production significantly reduced.
5.) allows more complete and efficient conversion of the CO and hydrogen.

In a typical laboratory unit the slurry is preferably stirred to promote good mixing to avoid catalyst settling and to reduce mass transfer limitations between gas and liquid. A rate of stirring is generally in the range of about 600 to 1200 rpm for laboratory sized turbines.

The reactor is typically purged with $N_2$ (or other inert gas) prior to introduction of syngas to remove any reactive gases and heated to reaction temperature prior to introduction of the $CO/H_2$.

The $H_2/CO$ molar ratio is preferably in a molar ratio of 10:1 to 1:10, preferably 3:1 to 0.5:1, and especially 1:1 to 2:1. Temperatures are generally in the range of about 190° C. to 300° C., preferably about 220° C. to 240° C. Higher temperatures can be used but tend to cause production of lighter products. Lower temperatures tend to result in lower rates and increased heavy wax formation. Useful reaction pressure is in the range of about 50 to 650 psig, and preferably about 150 to 650 psig. Space velocity is generally about 100 to 15000 volumes of gaseous fed per volume of dry catalyst in the slurry per hour, and preferably in the range of about 5000 to 15,000 v/v/hr. Higher space velocities lower CO conversion.

Carbon monoxide conversions are generally about 50%, in each of one or more stages. Preferably, the reaction variables are adjusted to minimize carbon dioxide and methane production and to maximize selectivity to $C_5$ plus paraffins while achieving good catalyst activity maintenance.

Generally, a typical preferred mode of operation for testing catalysts in a laboratory is a continuous stirred tank reactor (CSTR) using a highly paraffinic wax as the slurry liquid; a catalyst/liquid ratio of about 100 grams per liter; stirring the reactor turbine at 1,200 rpm; an $H_2/CO$ ratio of about 2:1; temperature of about 230° C.; pressure of about 300 psig, and space velocity of about 5000 v/v/hr using syngas feed.

Effluent reactant gases from the process may be separated and recycled, if desired, for further hydrocarbon synthesis. Industrial methods of collecting the products are well known and include fractional distillation and the like. Auxiliary equipment is conventional and known to those skilled in the art.

In a two stage (two reactor) process configuration hydrocarbon product and water are removed from the effluent of the first reactor and the CO/H2 mixture introduced to the second reactor, with its effluent being separated and processed as described above.

For laboratory testing, feed carbon monoxide syngas is purified and blended with hydrogen or hydrogen and diluent gas. The blend components are metered into the reactor containing the catalyst slurry. Effluent vapor from the reactor is passed through a sequence of condensation traps: a first wax trap maintained at about 200° C.; a second wax trap maintained at about 100° C. and an oil trap maintained at about 0° C. The remaining gas is passed through a gas meter and to a chromatographic column for analysis or collected for analysis at a later time. Laboratory test conditions are summarized below:

| | |
|---|---|
| Temperature: C. | 190–300 |
| Synthesis Gas Pressure: psig | 60–565 |
| Space Time(*): g cat./N1/hr | 0.1–5 |
| $H_2$/CO mole ratio | 0.6–2 |

(*)Expressed as normal liters of carbon monoxide feed

Treatment of Results

In order to normalize catalyst activity data obtained at somewhat different reactor conditions in a continuous stirred tank reactor, kinetic equations are used to calculate relative activity as follows:
The kinetic model used is $$K\theta = \frac{X(1 + \alpha X)}{(1 - X)} \text{ where}$$

$K$ = a kinetic parameter with the units of reciprocal space time, and which is proportional to hydrogen partial pressure in the feed gas to the power of 0.6 and to the relative activity ($RA$) of the catalyst $\theta$ = fraction conversion of carbon monoxide in the reactor, expressed as $\frac{(\text{feed CO} - \text{product CO})}{\text{feed CO}}$ where the CO is expressed in moles per hour $\alpha$ = the contraction factor for the reaction system.

$(2 H_2)_g + (CO)_g = -(CH_2) -_l + (H_2 O)_g$ and is equal to $-0.66$.

Hydrocarbon selectivities are expressed on a carbon atom basis, as the percentage of converted CO which appears as a given product. For example:

$C_5$ + Selectivity: % =

$$\left[ \frac{\text{Carbon Yield for all } C_5 + \text{hydrocarbons}) \times 100}{\text{Carbon conversion}} \right] \text{ or}$$

$100 - 100 \times$ (sum fractional selectivities to $C_1$, $C_2C_3$ and $C_4$)

This selectivity term used does not include the carbon converted to carbon dioxide.

The "Schulz-Flory alpha" is a known method for describing the product distribution in Fischer-Tropsch synthesis. The Schulz-Flory alpha is the ratio of the rate of chain propagation to the rate of propagation plus termination and is described from the plot of in (Wn/n) vs. n, where Wn is the weight fraction of products with a carbon number of n. The alpha value is thus indicative of the selectivity of the catalyst for producing heavy hydrocarbons from synthesis gas.

ILLUSTRATIVE EMBODIMENTS

Catalyst and Support Characterization

Catalyst and support surface area and pore volume were determined by methods well known in the art. Surface area was measured by the BET method, while pore volume was determined either by the nitrogen adsorption method or by mercury intrusion. A summary of catalyst support properties in shown in Table 2.

Catalyst Reduction

Prior to determination of the Fischer-Tropsch synthesis catalyst activity, a sample of each catalyst, in the form of microspheres of a typical size of between 38 and 106 microns, as pre-reduced in a fluidized bed reduction apparatus. Hydrogen was passed into the reduction unit at a superficial velocity of 1 ft/sec (10.8 cu ft/hr) while heating the catalyst at a rate of 1° C./min to 350° C. This temperature was then maintained for 14 hours before cooling and discharging the catalyst under a nitrogen atmosphere. The reduced catalyst was weighed at this point. A suitable amount of the reduced catalyst was mixed with about 300 g (about 400 ml) of Synfluid (Chevron Synfluid No. 8) and added to the autoclave for measurement of its Fischer-Tropsch conversion activity.

Hydrocarbon Synthesis Procedure

A stirred autoclave reactor of 1 liter total volume was employed with continuous gas flow to determine the catalyst activity for Fischer-Tropsch conversion of synthesis gas at a system pressure in the range of 175 to 350 psig. An $H_2$/CO molar ratio in the range of 1.7 to 2.2 was used at a total flow rate in the range of about 90 to 200 liters per hour. Catalyst charge weights were in the range of 30 to 50 grams in 500 ml reaction volume. Gas and liquid products were analyzed by chromatographic procedures. Product was collected for analysis to provide data for yields, conversions and material balance.

EXAMPLE 1

A solution of cobalt nitrate, $Co(NO_3)_2 \cdot 6H_2O$, was dissolved in 49.2 ml distilled water. This solution was then added, with stirring, to 50.0 g of Vista Catapal alumina, which is a psuedoboehmite type alumina, which had been first calcined at 500° C. for 6 hours. An additional 63 ml of distilled water was added to provide excess liquid over the alumina. The excess liquid was then evaporated at 66° C. and the sample dried at 104° C. for 6.3 hours. The dried catalyst was then calcined in air at 500° C. for a period of 3.3 hours. The calcined catalyst was screened to provide a 38 –75 micron fraction to the reduction unit. The final catalyst contained 16.7 wt. % cobalt. The Fischer-Tropsch conversion results are contained in Table 1.

EXAMPLE 2

A solution of cobalt nitrate was prepared by adding 49.4 g cobalt nitrate to 41.0 g water. This solution was added to 40.0 g of LaRoche VERSAL-900 alumina. The solution volume was in excess of the incipient wetness point. The excess liquid was evaporated on a hot plate and the catalyst transferred to an oven at 95° C. and dried overnight. The final catalyst was screened to a 38–106 micron fraction. The final cobalt content was 20.0 wt % on a water free basis. The Fischer-Tropsch conversion results are contained in Table 1.

EXAMPLE 3

A solution of cobalt nitrate containing 123.5 g of cobalt nitrate and 126 ml water was prepared and added to 100 g of LaRoche VERSAL-900 alumina which had been first calcined at 500° C. for 2 hours. The wet catalyst was dried overnight at 102° C. A second impregnation was performed on the dried material using 120 ml of an aqueous solution of cobalt nitrate containing 87.2 g cobalt nitrate. The wet catalyst was dried again at 124° C. overnight. The final catalyst contained 35 wt. % cobalt on a water free basis. The catalyst was screened to a 38–106 micron fraction. The Fischer-Tropsch conversion results are contained in Table 1.

EXAMPLE 4

138.7 g of cobalt nitrate was added to a 20% aqueous solution of zirconium nitrate, $Zr(NO_3)_4.5H2O$, in an amount of 82.74 g, and the final volume made up to 132 ml. This solution was added to 100 g of LaRoche VERSAL-900 alumina which had been first calcined at 500° C. for 2 hours. An additional 12 ml of water was added to the catalyst. After about an hour, the catalyst was transferred to an oven and dried at 103° C. for about 8 hours. The final catalyst, which contained 2.5 wt. % Zr and 20.0 wt. % cobalt on a water free basis, was screened to a 38–106 micron fraction. This sample was designated Example 4a.

A portion of the dried catalyst of Example 4a was calcined in air by heating to 300° C. over a period of 2 hours, holding at this temperature for 1 hr and then heating to about 495° C. over a period of 1 hour, at which point the power to the calciner was turned off and the catalyst allowed to cool overnight. This sample was designated Example 4b. The Fischer-Tropsch conversion results for both Examples 4a and 4b are contained in Table 1.

EXAMPLE 5

Ammonium molybdate, 8.1 g, was dissolved in 60° C. water and made up to 150 ml. The molybdenum solution was then added to 125 g of VERSAL-900 previously calcined at 500° C. for 2 hours. The wet molybdenum-alumina was dried at 100° C. for 4 hours and then impregnated with a solution of 174.3 g of cobalt nitrate made up to 145 ml. The catalyst was dried at 100° C. overnight. The final catalyst contained 2.5 wt. % Mo and 20 wt. % cobalt on a water free basis. The Fischer-Tropsch conversion results are contained in Table 1.

Catalysts prepared in Examples 2, 3, 4 (part 1) and 5 were hydrogen calcined and reduced at 350° C.

EXAMPLE 6

(Prophetic Example)

A catalyst can be made by adding about 70 g of cobalt nitrate and about 3.25 g of ammonium molybdate to 83 grams of a 20% solution of $Zn(NO_3)_4.5H2O$ and making up the volume with distilled water to 150 ml. This solution is added to 100 g of LaRoche Versal-900 alumina that has been calcined at 500 C. for about 2 hours. After about an hour the alumina wet with the solution is dried in an oven at about 100 C. for 8 to 10 hours. The resulting catalyst will contain about 20% wt. cobalt, 1.25% wt. zirconium and 1.25% wt. molybdenum. If this catalyst is tested for production of hydrocarbons by the procedure outlined under the heading "HYDROCARBON SYNTHESIS PROCEDURE" the results will be as shown in Table 1.

EXAMPLE 7

A commercially available cobalt-molybdenum catalyst, Crosfield 465, was ground and screened to a particle size range of 15·to 106 microns. The manufacturer quotes the typical cobalt and molybdenum contents as 3.8 weight % and 12.3 weight % respectively. This catalyst was tested in the same way as the catalysts of the other examples. The results of testing are shown in Table 1. This catalyst is a typical HDS (hydrosulfurization) catalyst.

Discussion of Test Results

Tables 1 and 3 summarize the results of Examples 1 through 7. The catalysts of Examples 1 through 3 illustrate the effectiveness of catalysts with about 16% to 35% cobalt supported on various alumina supports.

When compared to the catalysts of Examples 1 and 2, the catalyst of Example 5 shows an unexpected improvement in activity when 2.5 wt. % molybdenum is included in the composition. Reference to Table 1 demonstrates an unexpected improvement in activity, as expressed by the relative rate of reaction of carbon monoxide (as defined above in the "Treatment of Results" section). The activity of the catalyst of Example 5 is between 56% and 70% higher than that of the prior art type catalysts of Examples 1 and 2, which contain only cobalt at about the same level as that of Example 4.

The catalyst results of Example 3 show that 35% cobalt must be added to the alumina in order achieve a 70% improvement in activity.

In example 7 a commercial Co—Mo catalyst is shown to have no activity for Fischer-Tropsch.

When 2.5 wt. % zirconium is incorporated with cobalt, as represented by Examples 4a and 4b, an unexpected improvement in activity occurs, as expressed by the relative rate constant (as defined in the "Treatment of Results" section) which is a measure of catalyst activity. Thus, when the catalysts of Examples 4a and 4b are compared with those of Examples 1 and 2, which contain a similar amount of cobalt but no zirconium, it is seen that the relative activity of the catalysts of this invention are higher by a factor of about 2 over catalysts without zirconium. This significantly shows the unexpected results and an advantage of the catalysts of the present invention.

A mixed promoter catalyst having the same cobalt content and with 1.25% molybdenum and 1.25% zirconium would be more active than one with molybdenum alone and almost as active as with zirconium. This is illustrated in the prophetic example 6. This catalyst would be nearly twice as active as un-promoted cobalt catalyst.

The catalysts of Example 4a and 4b differ in that Catalyst 4a was dried at 103 C. and hydrogen calcined and reduced at 350 C., whereas Catalyst 4b was calcined in air at 495 C. before reduction at 350 C. Further, reference to Table 1 shows that the catalysts of Example 4 show an unexpected improvement in $C_5$ plus product selectivities when zirconium is included in the composition. Specifically, the selectivity for the formation of desirable liquid hydrocarbons, as expressed by the $C_5+$ selectivity, is unexpectedly improved while at the same time the amount of less desirable oxygen-containing products such as methanol and ethanol was unexpectedly decreased. Further examination of Table 1 and 3 demonstrates a further unexpected result. The Schulz-Flory alpha values determined from a carbon-number distribution obtained by analysis of wax were higher for zirconium-containing catalysts.

The Schulz-Flory alpha value is defined as the probability of chain growth step to the next higher carbon number divided by the sum of the growth step probability plus the chain termination probability. This parameter can be used to estimate the distribution of carbon number products and thereby the effectiveness of the process to make liquid products with a particular carbon number distribution.

Alpha values in experimental systems depend on the nature of the catalyst and on the fundamental operating conditions to which the catalyst is exposed. As a consequence, evaluation of differences between different catalysts must be done at a common set of operating conditions. Catalysts were accordingly compared at a common set of conditions herein. Alpha values based on analysis of products from six separate tests are included in Tables 1 and 3. The alpha values refer to two kinds of measurements for each catalyst test.

One alpha is determined from the analysis of the reactor wax, which is that hydrocarbon remaining in the reactor at the end of the test period. This represents a distribution.

The other alpha values were obtained from the analysis of a proportional collection of products obtained near the end of the test period. The liquid products were blended and analyzed. These alphas were taken from carbon numbers in a range lower than that of the starting liquid, i.e., lower than 30.

The average alpha value for the two tests employing catalysts of this invention (Examples 4a and 4b ) is 0.88, which is significantly higher than the average alpha value of 0.84 obtained with the catalysts of Examples 1 and 2, which are catalysts with similar levels of cobalt but no zirconium. Similar results are predicted for the catalyst of Example 6. Thus, the alpha values, which are a direct indication of the yield of $C_5$ plus liquid products having boiling points in the range of the most desirable products, namely gasoline and diesel, are unexpectedly the highest when zirconium is incorporated with cobalt.

The data contained in Tables 1 and 3 shows that, when the catalysts of Examples 1, 2, 4a and 4b are compared, the addition of zirconium results in a $C_5$ plus selectivity of 86.1 to 84.6% compared to 79.1 and 80.0% with no zirconium. This improvement in selectivity is quite significant. Similarly the methane selectivities for the zirconium catalysts are much lower; this is also advantageous.

This same advantageous result would result from the use of a mixed promoter—molybdenum and zirconium catalyst. Thus, a catalyst having the same cobalt content and with 1.25% zirconium and 1.25% molybdenum would be more active and more selective for $C_5$ plus products than unpromoted cobalt catalysts or catalysts promoted with molybdenum alone. Any ratio of zirconium to molybdenum will have an advantageous effect, but Zr/Mo ratios above 2 are especially desirable.

TABLE 1

SUMMARY OF CATALYST PERFORMANCE FOR FISCHER-TROPSCH SYNTHESIS IN A CONTINUOUS STIRRED TANK REACTOR
Temperature = 230 C., Hydrogen/CO mole ratio = 2

| Example | 1 | 2 | 3 | 4a | 4b | 5 | 6[7] | 7 |
|---|---|---|---|---|---|---|---|---|
| Support Type[1] | Catapal Al | V900 Al | V900 Al | V900 Al | V900 Al | V900 Al | V900 Al | HDS Co/Mo |
| Metals | | | | | | | | |
| Co % | 16.7 | 20 | 35 | 20 | 20 | 20 | 20 | 3.8 |
| Mo % | | | | | | 2.5 | 1.25 | 12.3 |
| Zr % | | | | 2.5 | 2.5 | | 1.25 | |
| Pressure, psig | 250 | 250 | 200 | 175 | 200 | 175 | 200 | 250 |
| Cat. wt. g. | 44.8 | 38.6 | 40.9 | 37.6 | 30.3 | 28.6 | 30 | 3.8 |
| GAS rate, Nl/hr | 135 | 135 | 201.4 | 135 | 135 | 135 | 135 | 24 |
| Nl/hr/g cat | 3.0 | 3.5 | 4.95 | 3.59 | 4.46 | 4.72 | 4.5 | 3.14 |
| Time on Line, 24 hr | | | | | | | | |
| CO Nl/hr | 45 | 45 | 65 | 45 | 45 | 45 | 45 | 45 |
| CO conv. | 68.4 | 62.0 | 65.0 | 77.2 | 66.5 | 62.6 | 65 | 3.8 |
| $CH_4$ sel. % | 8.7 | 9.4[3] | 8.3 | 6.6 | 7.1 | 9.7 | 6.5 | |
| $CO_2$ sel. % | 2.7 | 2.8[3] | 3.0 | 5.6 | 2.8 | 3.7 | 4 | |
| Kθ | 1.2 | 0.96 | 1.53 | 1.7 | 1.2 | 0.98 | 1 | |
| Kθ corr[5] | 1.06 | 0.84 | 1.53 | 1.83 | 1.2 | 1.65 | | |
| Rel Activity | 1.08 | 1.00 | 1.71 | 2.08 | 1.82 | 1.68 | 1.8 | |
| C5 sel. %[4] | 79.1[2] | 80.0[3] | 83.3 | 86.1 | 84.6 | 81.0 | 85 | |
| Alpha[6] | 0.832 | 0.847 | 0.864 | 0.851 | 0.916 | 0.806 | 0.85 | |
| @ hour | 216 | 168 | 288 | 120 | 96 | 120 | 120 | |

[1]Al = alumina; V = VERSAL
[2]Data after 72 hours & 60% conversion
[3]Data after 48 hours & 62% conversion
[4]At 24 hours
[5]Corrected to 215 psia by ratio of pressures to 0.6 power
[6]Based on reactor wax analysis near end of run
[7]Hypothetical example

TABLE 2

PHYSICAL PROPERTIES OF CATALYST SUPPORTS

| Support | VERSAL-900 | CATAPAL |
|---|---|---|
| Support Analysis | | |
| Calcination temp. C. | 500 | 500 |
| Calcination time, hr. | 2 | 6 |
| Surface area m2/g | 221 | 236 |
| Mercury pore vol. ml/g | 0.483 | 0.376 |

TABLE 3

| SUMMARY OF ALPHA VALUES Temperature = 230 C., H$_2$/CO mole Ratio = 2 | | | | | | | |
| --- | --- | --- | --- | --- | --- | --- | --- |
| Example | 1 | 2 | 3 | 4a | 4b | 5 | 6[3] |
| Support Type[1] | Catapal Al | V900 Al | V900 Al | V900 Al | V900 Al | V900 Al | V900 Al |
| Metals | | | | | | | |
| Co % | 16.7 | 20 | 35 | 20 | 20 | 20 | .20 |
| Mo % | | | | | | 2.5 | 1.25 |
| Zr % | | | | 2.5 | 2.5 | | 1.25 |
| Pressure, psig | 250 | 250 | 200 | 175 | 200 | 175 | 200 |
| Cat. wt. g. | 44.8 | 38.6 | 40.9 | 37.6 | 30.3 | 28.6 | 30 |
| GAS rate, Nl/hr | 135 | 135 | 201.4 | 135 | 135 | 135 | 135 |
| Nl/hr/g cat | 3.0 | 3.5 | 4.95 | 3.59 | 4.46 | 4.72 | 4.5 |
| CO Nl/hr | 45 | 45 | 65 | 45 | 45 | 45 | 45 |
| ALPHA[1] | 0.832 | 0.847 | 0.864 | 0.851 | 0.916 | 0.806 | 0.85 |
| @ hour | 216 | 168 | 288 | 120 | 96 | 120 | — |
| Carbon No. Range | 20–58 | 50–66 | 45–74 | 50–70 | 55–65 | 50–60 | — |
| ALPHA[2] | 0.82 | 0.79 | 0.844 | 0.79 | 0.824 | 0.81 | 0.8 |
| @ hour | 216 | 168 | 192 | 120 | 96 | 120 | — |
| Carbon No. Range | 9–14 | 10–15 | 9–18 | 4–15 | 9–17 | 9–15 | — |

[1]Based on analysis of Reactor Wax near end of the run
[2]Based on analysis of Products
[3]Hypothetical example These representative embodiments are illustrative of the invention, but other modifications and variations are within the scope of the following claims.

What is claimed is:

1. A catalyst useful for Fischer-Tropsch synthesis by conversion, at reaction conditions, of a mixture of carbon monoxide and hydrogen to hydrocarbons predominately in the carbon number range of C$_5$ plus in a slurry catalytic reaction process, said catalyst comprising from about 2% to 35% by weight, based on the total weight of catalyst, cobalt and from about 0.1% to 10% by weight of a metal component or components selected from the group consisting of zirconium, molybdenum and both zirconium and molybdenum supported on an alumina support wherein the alumina support is an is an anhydrous alumina derived from LaRoche VERSAL alumina, and is in the form of microspheres.

2. The catalyst of claim 1, wherein the catalyst comprises from about 10% to 20% cobalt and from about 1% to 5% by weight zirconium, or molybdenum or a combination of zirconium and molybdenum.

3. The catalyst of claim 1, wherein the support that has a surface area of at least about 45 m$^2$/g and a pore volume of at least about 0.3 cm$^3$/g.

4. A catalyst useful for Fischer-Tropsch synthesis by conversion, at reaction conditions, of a mixture of carbon monoxide and hydrogen to hydrocarbons predominately in the carbon number range of C$_5$ plus in a slurry catalytic reaction process, said catalyst comprising from about 2% to 35% by weight, based on the total weight of catalyst, cobalt and from about 0.1% to 10% by weight of a metal component or components selected from the group consisting of zirconium, molybdenum and both zirconium and molybdenum supported on an alumina support which catalyst contains cobalt, zirconium and molybdenum and is supported on microspheres of alumina.

5. The catalyst of claim 4, wherein the catalyst comprises from about 10% to 25% cobalt, from about 0.5% to 5% zirconium and from about 1% to 5% molybdenum, the weight ratio of zirconium to molybdenum being above about 2.

6. The catalyst of claim 4, wherein the alumina has a surface area above 50 m$^2$/g and a pore volume of at least about 0.4 cm$^3$/g and the molybdenum to zirconium ratio is about 0.5 molybdenum to 1 zirconium by weight.

7. The catalyst of claim 6, wherein the alumina is in the form of microspheres having particle diameters in the range of 5 to 100 microns and has a surface area of at least about 50 m$^2$/g and a pore volume of at least about 0.4 cm$^3$/g.

8. The catalyst of claim 4 wherein the catalyst support is a pseudoboehmite alumina and is in the form of microspheres having particle diameters in the range of 5 to 250 microns.

9. The catalyst of claim 8, which contains cobalt, zirconium and molybdenum and is supported on microspheres of calcined LaRoche VERSAL alumina.

10. The catalyst of claim 4 wherein the catalyst support is a calcined pseudoboehmite alumina and is in the form of microspheres having particle diameters in the range of 5 to 250 microns.

11. The catalyst of claim 4 in which the catalyst comprises from about 10% to 25% cobalt, from about 0.5% to 5% zirconium and from about 1% to 5% molybdenum, the weight ratio of zirconium to molybdenum being above about 2.

12. A catalyst useful for the conversion at reaction conditions of synthesis gas to hydrocarbons with selectivity to C$_5$ plus above about 80% in a slurry catalytic reaction process that comprises, cobalt, zirconium and molybdenum on an alumina support, said catalyst containing from about 10% to 25% cobalt, from about 1% to 5% molybdenum and from about 0.5% to 5% zirconium, based on the total weight of the catalyst, the weight ratio of molybdenum to cobalt being below about 0.150.

13. The catalyst of claim 12 wherein the weight ratio of molybdenum to cobalt is below about 0.125.

14. The catalyst of claim 12 wherein the alumina is in the form of microspheres having particle diameters in the range of 5 to 250 microns.

15. The catalyst of claim 12 wherein the alumina support is homogeneously co-impregnated with said cobalt and zirconium from a common aqueous solution of water soluble salts of the cobalt and zirconium metal components.

* * * * *